United States Patent
Gao

(10) Patent No.: US 8,919,228 B1
(45) Date of Patent: Dec. 30, 2014

(54) PRECISION RATCHETING MECHANISM FOR GRIPPING DEVICE

(76) Inventor: Hua Gao, Fox Point, WI (US)

(*) Notice: Subject to any disclaimer, the term of this patent is extended or adjusted under 35 U.S.C. 154(b) by 423 days.

(21) Appl. No.: 13/448,225

(22) Filed: Apr. 16, 2012

Related U.S. Application Data

(63) Continuation-in-part of application No. 12/380,823, filed on Mar. 4, 2009, now Pat. No. 8,393,254.

(51) Int. Cl.
*B25B 7/14* (2006.01)
*A61B 17/00* (2006.01)

(52) U.S. Cl.
CPC ........................................ *A61B 17/00* (2013.01)
USPC .................... 81/338; 81/320; 81/323; 81/335

(58) Field of Classification Search
USPC ......... 81/318, 324, 329, 338, 177.9; 606/208, 606/205
See application file for complete search history.

(56) References Cited

U.S. PATENT DOCUMENTS

| | | | | |
|---|---|---|---|---|
| 765,328 A | * | 7/1904 | Stripe | 140/52 |
| 838,514 A | * | 12/1906 | Baker | 81/320 |
| 1,092,050 A | * | 3/1914 | Hoiser | 81/323 |
| 1,427,668 A | * | 8/1922 | Williams | 81/335 |
| 2,688,351 A | | 9/1954 | Sweet et al. | |
| 3,039,337 A | * | 6/1962 | Stuart-Prince | 72/409.11 |
| 3,510,923 A | | 5/1970 | Blake | |
| 4,475,544 A | | 10/1984 | Reis | |
| 4,896,661 A | | 1/1990 | Bogert et al. | |
| 6,212,977 B1 | * | 4/2001 | Liou | 81/323 |
| 6,551,316 B1 | * | 4/2003 | Rinner et al. | 606/57 |
| 6,635,072 B1 | | 10/2003 | Ramamurti et al. | |
| 7,306,212 B2 | | 12/2007 | Cantin | |
| 7,625,391 B2 | | 12/2009 | Kebel et al. | |

OTHER PUBLICATIONS

U.S. Appl. No. 12/380,823, filed Sep. 10, 2009, Gua, Hua.
U.S. Appl. No. 11/526,526, filed Oct. 11, 2007, Randall, Peter.

* cited by examiner

*Primary Examiner* — Monica Carter
*Assistant Examiner* — Melanie Alexander
(74) *Attorney, Agent, or Firm* — Absolute Technology Law Group, LLC

(57) ABSTRACT

A gripping device with a precision ratcheting mechanism includes an upper and a lower arm, each terminating in a U-shaped receiver, connected by a pair of pivotal joints. A pawl device is pivotally connected to the U-shaped receiver of the upper arm, while a post, passing through the pawl device, is pivotally connected to the lower arm. The post contains a plurality of teeth on one surface and a teeth-engaging member in the pawl device contains a plurality of corresponding teeth which engage the teeth on the post. The teeth are disengaged by pressing a release surface, which compresses a spring and physically moves the teeth-engaging structure away from the post, allowing the post to move freely within the pawl device.

20 Claims, 9 Drawing Sheets

PRECISION RATCHETING MECHANISM FOR GRIPPING DEVICE

CROSS REFERENCE TO RELATED APPLICATIONS

This application is a continuation-in-part application of U.S. application Ser. No. 12/380,823 filed Mar. 4, 2009 now U.S. Pat. No. 8,393,254 entitled "Gripping Device," which is hereby incorporated by reference in its entirety.

FIELD OF INVENTION

The present invention relates to the field of medical devices, and more specifically to a gripping device with ratcheting mechanism,

TERMS OF ART

Figure 1:
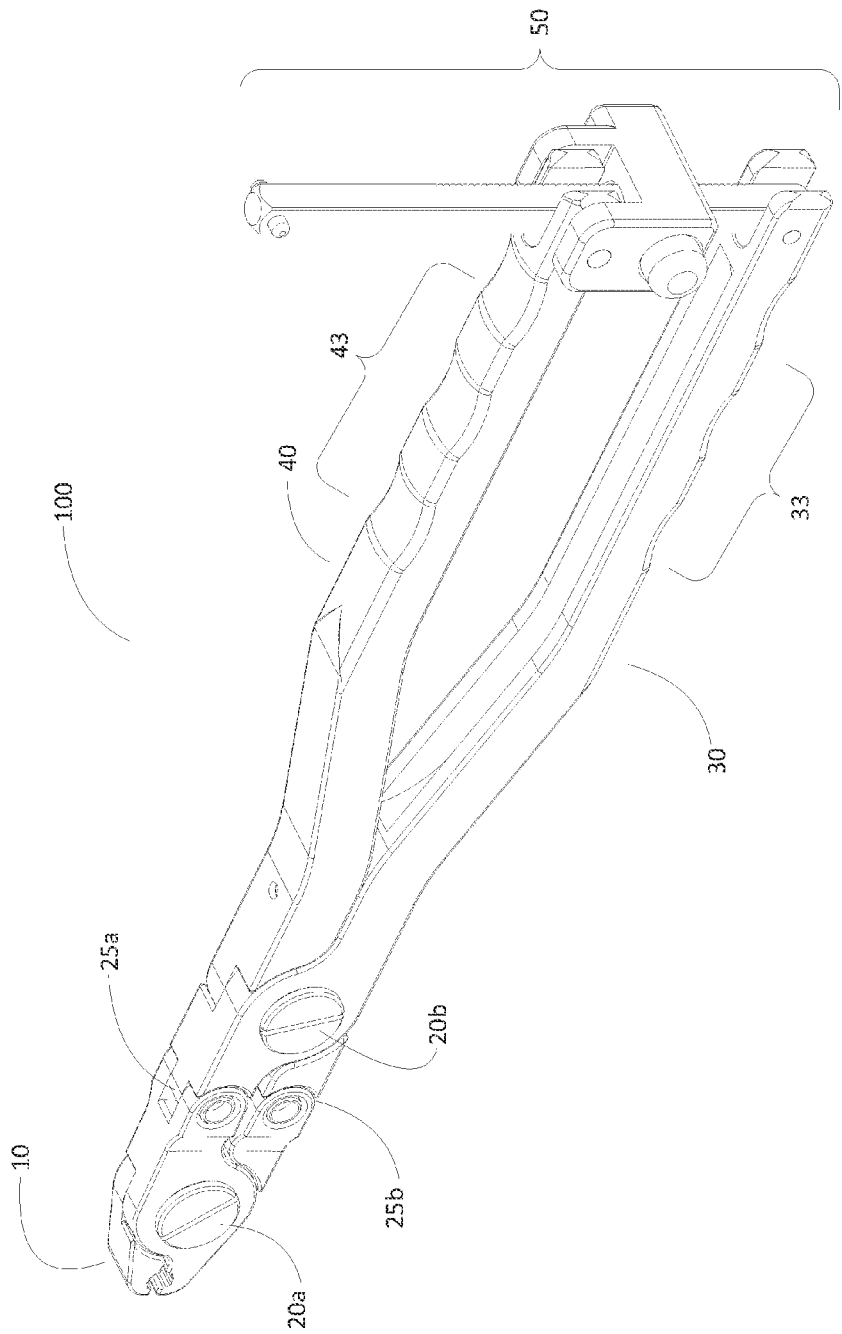
FIG. 1 is an exemplary embodiment of a gripping device.

As used herein, the term "gripping head" refers to any structure of device wh ch may be affixed to the end of an arm and which is capable of being secured on or around another object. Gripping heads may use friction, contours, compression or other forces to engage the other object.

As used herein, the term "gripping surface" refers to any contour, material, or structure which helps a user grasp a handle or arm. A gripping surface may include, but is not limited to, contours, ergonomic contours, rubber, silicon, textured surfaces, thinner or thicker portions, and combinations of these and other materials or structures known in the art to help users grasp a handle or arm.

As used herein, the term "hinged joint" refers to a connection between two solid objects permitting limited movement between them in only one plane.

As used herein, the term "pivotally connected" means having the ability to move about at least one axis while remaining secured.

As used herein, the term "U-shaped" refers to a structure with two ends having approximately parallel or actually parallel outward protuberances projecting in the same direction. A U-shaped structure may have curved or straight components, and transitions to the outward protuberances may be gradually curved or occur at distinct angles. Outward protuberances do not need to occur at 90 degrees.

BACKGROUND

Precision is a necessity for medical procedures and devices used for those procedures. Because medical devices are used to grab or grip very sensitive areas of the body, such as when working on arteries, veins, nerves or other very sensitive areas, devices must be able to be minutely adjustable, while still providing enough gripping strength.

Gripping devices must also be stably locked in a given position when the proper gripping strength is reached. If the device is not secured in position, the tool may tighten or loosing, potentially resulting in injury to a person or medical tool.

Accordingly, it is desirable to have a gripping device that has improved sensitivity and precision without affecting the gripping strength.

It is further desirable to have a gripping device which is easily locked into position and unlocked.

SUMMARY OF THE INVENTION

The present invention is a gripping device with a precision ratcheting mechanism. An upper and lower arm, each terminating in a U-shaped receiver, are connected by a pair of pivotal joints. A pawl device is pivotally connected to the U-shaped receiver of the upper arm, while a post, passing through the pawl device, is pivotally connected to the lower arm. The post contains a plurality of teeth on one surface and a teeth-engaging member in the pawl device contains a plurality of corresponding teeth which engage the teeth on the post. The teeth are disengaged by pressing a release surface, which compresses a spring and physically moves the teeth-engaging structure away from the post, allowing the post to move freely within the pawl device,

DETAILED DESCRIPTION OF INVENTION

For the purpose of promoting an understanding of the present invention, references are made in the text to exemplary embodiments of gripping device with ratcheting mechanism, only some of which are described herein. It should be understood that no limitations on the scope of the invention are intended by describing these exemplary embodiments. One of ordinary skill in the art will readily appreciate that alternate but functionally equivalent structures and materials may be used. The inclusion of additional elements may be deemed readily apparent and obvious to one of ordinary skill in the art. Specific elements disclosed herein are not to be interpreted as limiting, but rather as a basis for the claims and as a representative basis for teaching one of ordinary skill in the art to employ the present invention.

It should be understood that the drawings are not necessarily to scale; instead, emphasis has been placed upon illustrating the principles of the invention. In addition, in the embodiments depicted herein, like reference numerals in the various drawings refer to identical or near identical structural elements, FIG. 1 is an exemplary embodiment of gripping device 100. Gripping device 100 includes gripping head 10 at the front end of gripping device 100 and ratcheting mechanism 50 at the rear end of gripping device 100. Lower arm 30 and upper arm 40 are pivotally connected and pivot points 20a, 20b, with hinged joints 25a, 25b allow lower arm 30 and upper arm 40, respectively; to bend and open and close gripping head 10.

As illustrated, lower arm 30 and upper arm 40 have a bend at pivot points 20a, 20b, causing lower arm 30 and upper arm 40 to cross each other at pivot points 20a and 20b, such that hinged joint 25a, on lower arm 30, occurs above hinged joint 25b on upper arm 40.

In the exemplary embodiment described, pivot points 20a, 20b are illustrated as screws; however, in further exemplary embodiments, pivot points 20a, 20b may be any structure or device allowing lower arm 30 and upper arm 40 to move pivotally in relation to one another, including, but not limited to, screws, bolts, pins and other devices or structures which allow lower arm 30 and upper arm 40 to pivot with respect to one another.

As illustrated in FIG. 1, lower arm 30 and upper arm 40 each contain gripping surfaces 33, 44, respectively.

Figure 2:
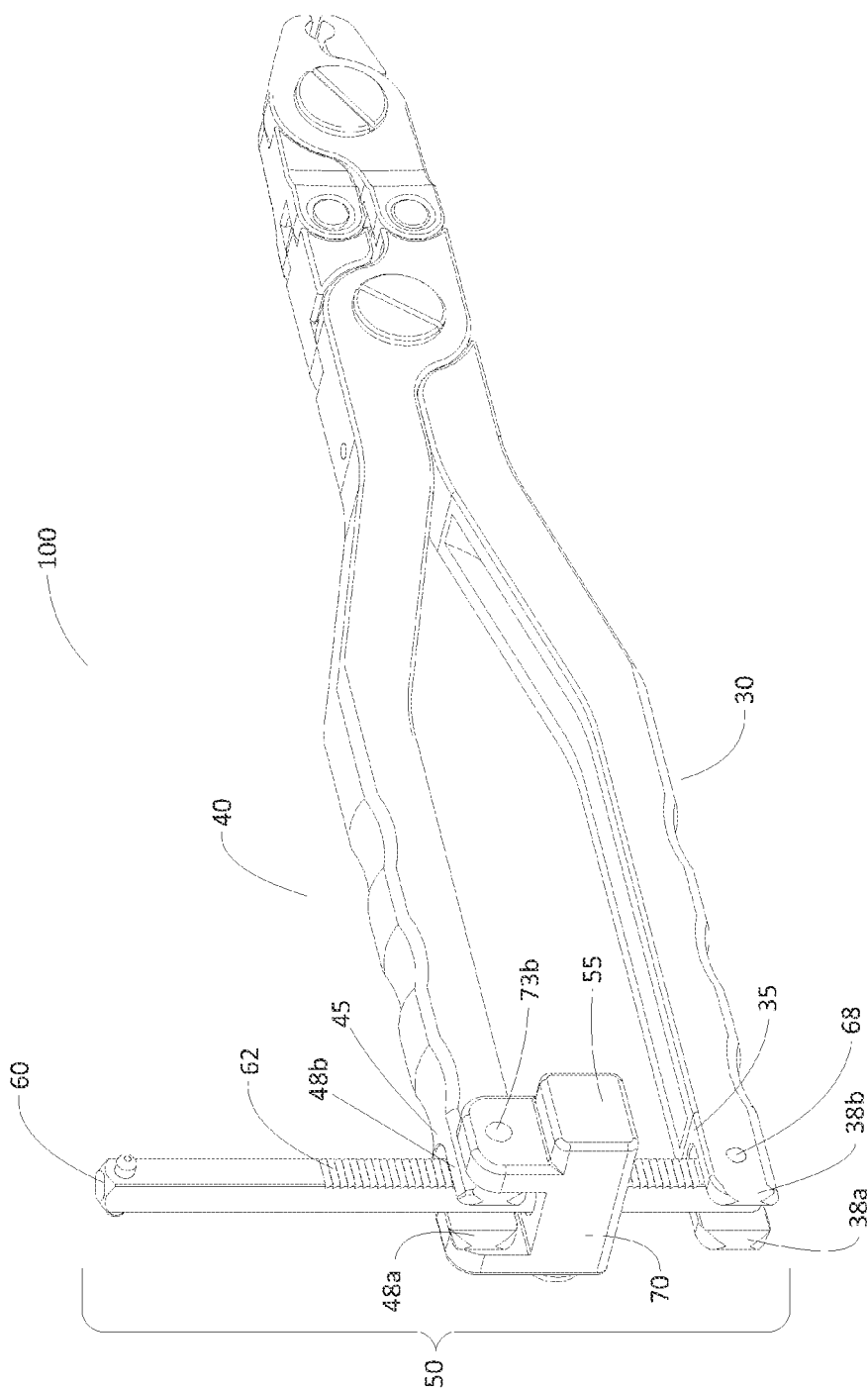
FIG. 2 is an exemplary embodiment of a gripping device.

FIG. 2 illustrates an exemplary embodiment of gripping device 100, showing teeth 62 on post 60 which interact with pawl device 70. Together post 60 and pawl device 70 create ratcheting mechanism 50 and join lower arm 30 and upper arm 40 at the rear of gripping device 100.

Post 60 is illustrated as square with teeth 62 along only a single rectangular surface of post 60. Teeth 62 cover approximately ⅔ of the distance of the single side of post 60. Teeth 62 are designed to engage pawl device 70 and are therefore required only along the distance of post 60 which may be engaged by pawl device 70.

In further exemplary embodiments, gripping device 100 may be configured to open and close to different distance, and post 60 may therefore be designed with teeth 62 over or less of its surface. In still further exemplary embodiments, post 60 may be a shape other than rectangular.

As illustrated in FIG. 2, lower arm 30 and upper arm 40 each terminate in U-shaped receivers 35, 45, respectively, which accept and secure post 60 between arms 38a, 38b and 48a, 48b, respectively. Arms 38a, 38b of U-shaped receiver 35 each contain an aperture (not shown), with a corresponding aperture 67 (not shown) passing through post 60. Pin 68 pivotally secures post 60 between arms 38a, 38b on lower post 30.

Similarly, arms 48a, 48b of U-shaped receiver 45 each contain an aperture (not shown), with corresponding apertures 72a, 72b (not shown) passing through pawl device 70. Pins 73a, 73b engage the apertures on arms 48a, 48b and apertures 72a, 72b to pivotally secure pawl device 70 to upper arm 40.

Figure 8A:
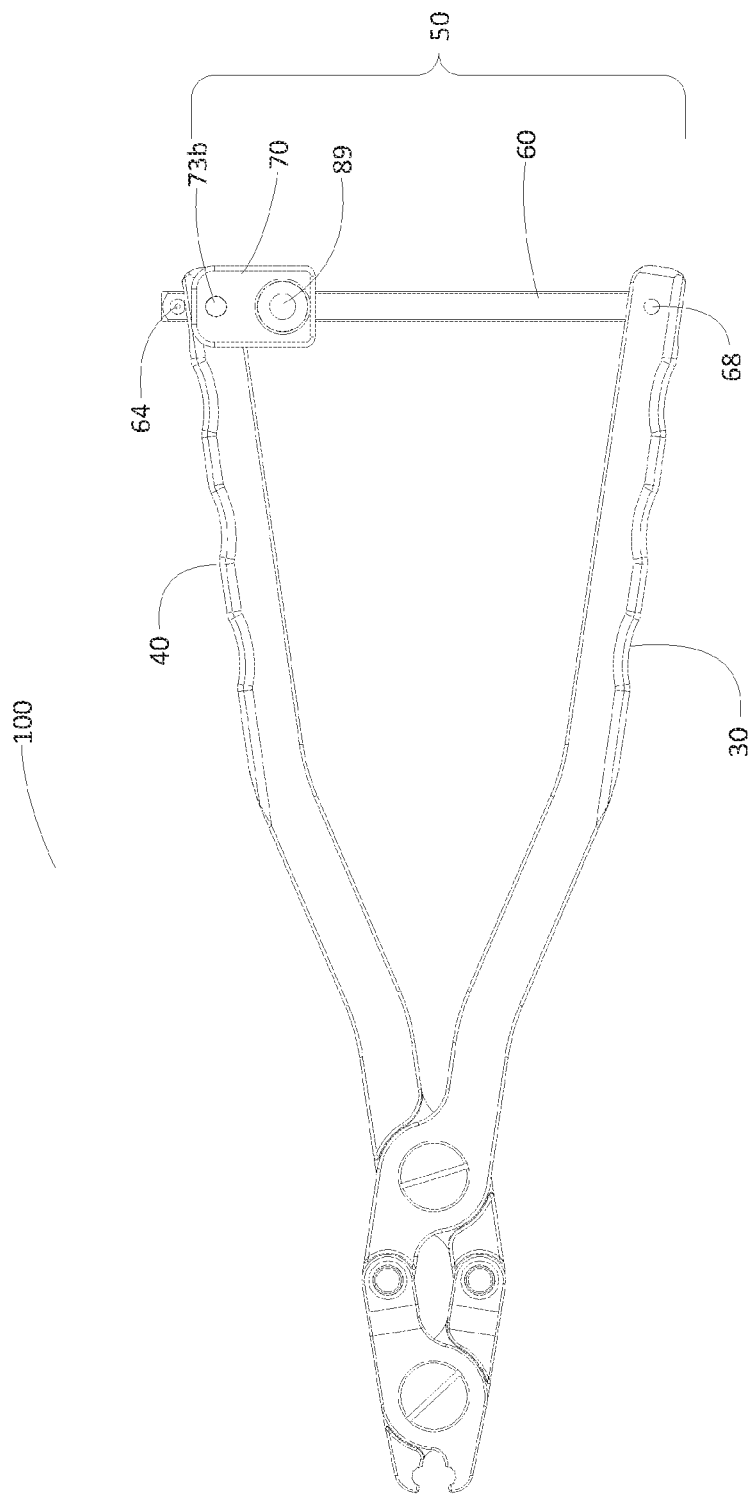
FIG. 8a illustrates an exemplary gripping device in open position.

As will be illustrated in FIGS. 8a and 8, it is essential that post 60 and pawl device 70 be pivotally attached to lower arm 30 and upper arm 40, respectively. Pivoting allows gripping device 100 to be opened and closed over a wider range. If post 60 and pawl device 70 were not pivotally connected to lower arm 30 and upper arm 40, respectively, post 60 would not be able to slide through pawl device 70.

In the exemplary embodiments shown, ratcheting mechanism 50 allows for precise adjustment of the spacing of lower arm 30 and upper arm 40. While ratcheting mechanism 50 is illustrated at the ends of lower arm 30 and upper arm 40, ratcheting mechanism 50 may be located anywhere along arms 30, 40. However, placing ratcheting mechanism 50 at the end of arms 30, 40 allows a wider range of precise adjustments.

Figure 3:
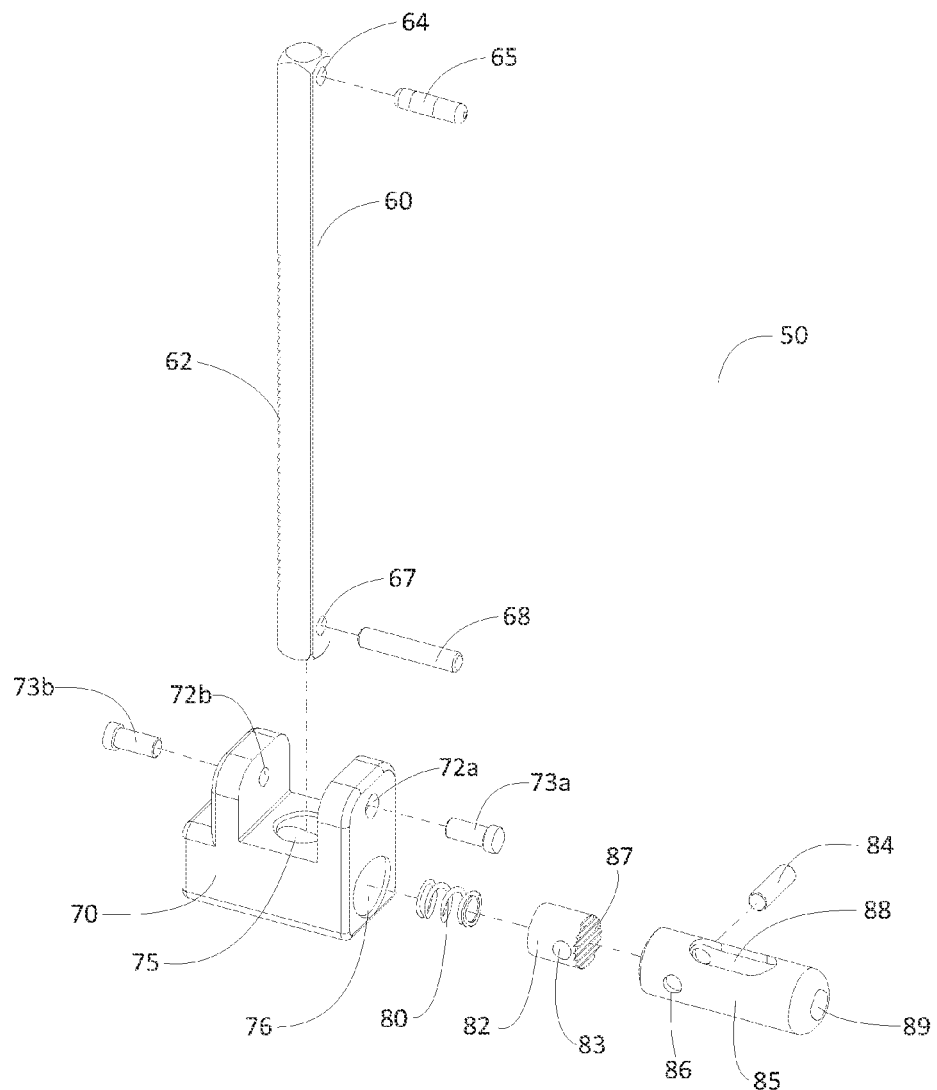
FIG. 3 is an exemplary embodiment of a ratcheting mechanism for a gripping device.
Figure 4:
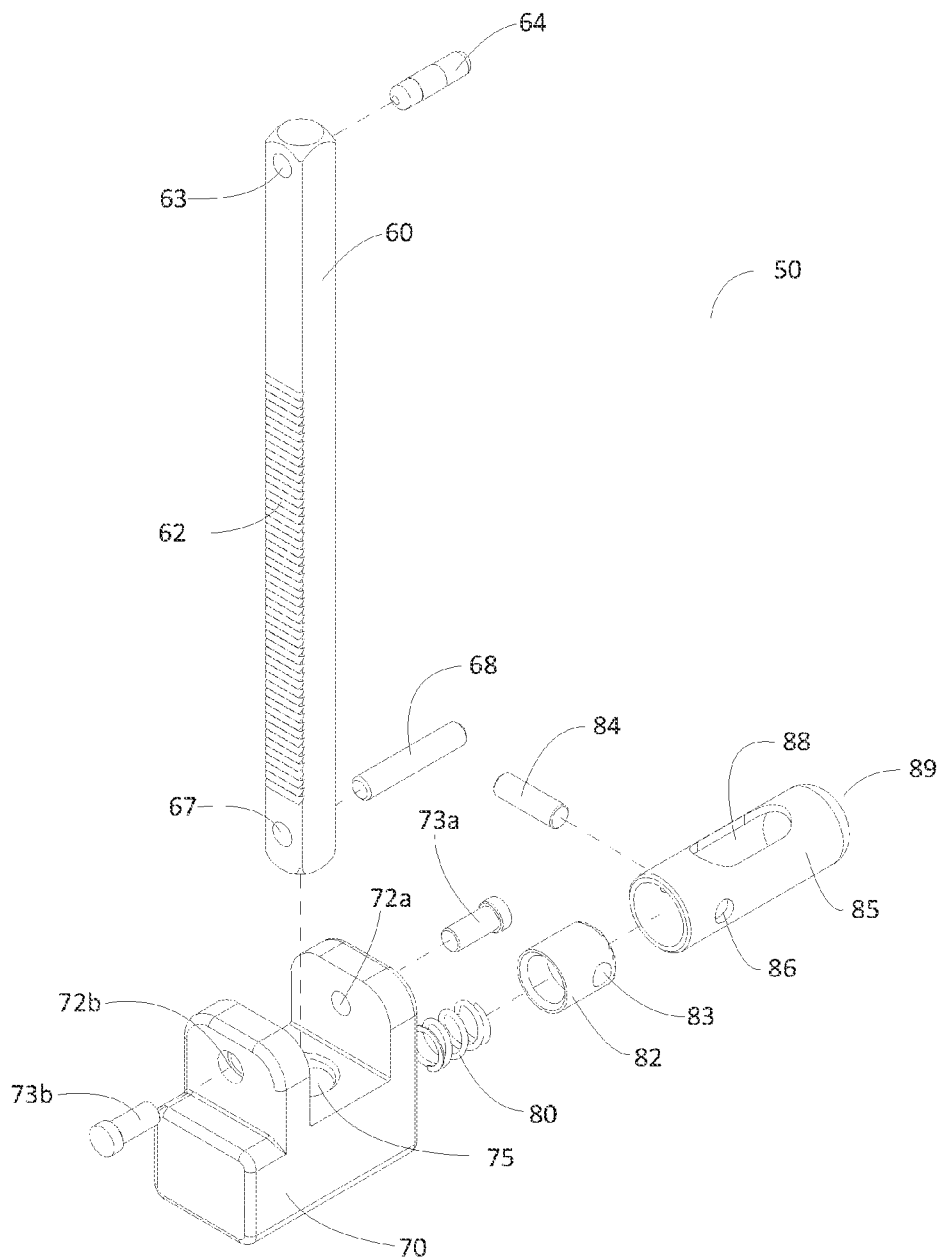
FIG. 4 is an exemplary embodiment of a ratcheting mechanism for a gripping device.

FIGS. 3 and 4 are exploded views of an exemplary ratcheting mechanism 50 for gripping device 100 (not shown). Ratcheting mechanism 50 includes post 60 with teeth 62, which connects to lower arm 30 (not shown) by pin 68, which passes through aperture 67 on the lower end of post 60. The upper end of post 60 includes aperture 63, which engages pin 64. Pin 64 protrudes from the upper end of post 60 to prevent post 60 from disengaging U-shaped receiver 45 of upper arm 40 (not shown).

In the exemplary embodiment shown, pawl device 70 is essentially U-shaped with a hollow central cavity. Apertures 72a, 72b on pawl device 70 are adapted to engage pins 73a, 73b, respectively, to pivotally attach pawl device 70 to upper arm 40 (not shown). Pawl device 70 also contains aperture 76, in which locking release shaft 85 is slidably engaged.

Locking release shaft 85 is a hollow tubular shaft which houses teeth-engaging structure 82. Pin 84 engages aperture 86 on locking release shaft 85 and aperture 83 on teeth-engaging structure 82 to secure teeth-engaging structure 82 within locking release shaft 85. Teeth-engaging structure 82 is also hollow and houses spring 80 when assembled with locking release shaft 85 in pawl device 70. Oblong aperture 88 goes all the way through locking release shaft 85 and aligns with aperture 75 of pawl device 70 when components are assembled. Aperture 75 also goes all the way through pawl device 70. Post 60 is therefore able to project through pawl device 70, and locking release shaft 85.

Release surface 89 projects from pawl device 70 when assembled, and teeth 87 of teeth-engaging structure 82 correspond to teeth 62 on shaft 60. As lower arm 30 (not shown) and upper arm 40 (not shown) of gripping device 100 are squeezed closer together (i.e., to grip a medical rod or other structure), upper arm 40 (not shown) with pawl device 70 slides downward along post 60, with post 60 and pawl device 70 pivoting appropriately so that post 60 is always perpendicular with pawl device 70. Teeth 62 engage teeth 87 to lock lower arm 30 (not shown) and upper arm 40 (not shown) in place with respect to each other.

When gripping device 100 (not shown) is at rest or gripping head 10 is being closed, spring 80 exerts an outward force against teeth-engaging structure 82, which, by using pin 84, keeps locking release shaft 85 pushed outward from pawl device 70. Post 60 projects through oblong aperture 88 near its inner edge, preventing locking release shaft 85 from being pushed out of pawl device 70.

To release arms 30, 40 (not shown) and open gripping head 10 (not shown), a user pushes on release surface 89, which compresses spring 80 and moves locking release shaft 85 inward towards pawl device 70. Teeth 87 disengage teeth 62, and post 60 may freely slide within apertures 88, 75. When release surface 89 is pressed inward, post 60 projects through oblong aperture 88 near its outer edge, providing a limit to how far locking release shaft 85 may be pushed into pawl device 70.

Figure 5:
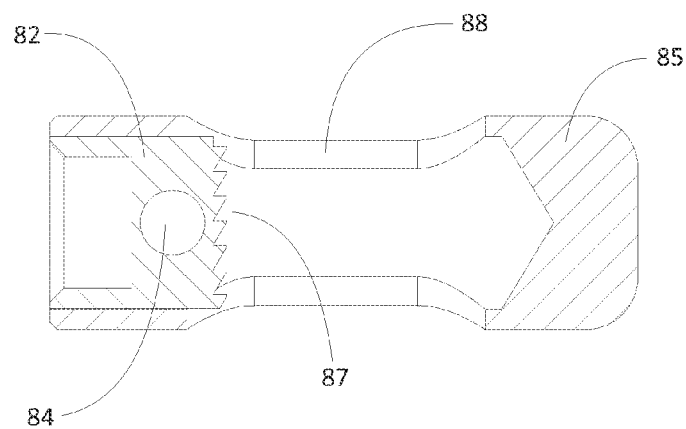
FIG. 5 illustrates an exemplary locking release shaft for a ratcheting mechanism for a gripping device.

FIG. 5 is a cross-section view illustrating locking release shaft 85 assembled with teeth-engaging structure 82. Pin 84 secures teeth-engaging structure 82 in locking release shaft 85. Oblong aperture 88 goes completely through locking release shaft 85. Oblong aperture 88 must be long enough to provide room for post 60 (not shown) to slide within oblong aperture 88 when locking release shaft 85 is pressed inward at a distance at which teeth 87 disengage teeth 62 (not shown) on post 60 (not shown).

Figure 6:
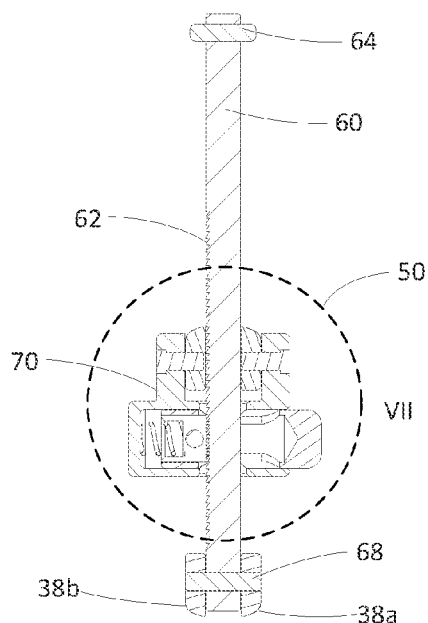
FIG. 6 is a cross sectional view of an exemplary ratcheting mechanism.

FIG. 6 is a cross sectional view illustrating an exemplary ratcheting mechanism 50 for gripping device 100 (not shown). Post 60 with teeth 62 passes completely through pawl device 70 and is pivotally secured between arms 38a, 38b with pin 68. Pins 68 and 64 pass completely through post 60.

Figure 7A:
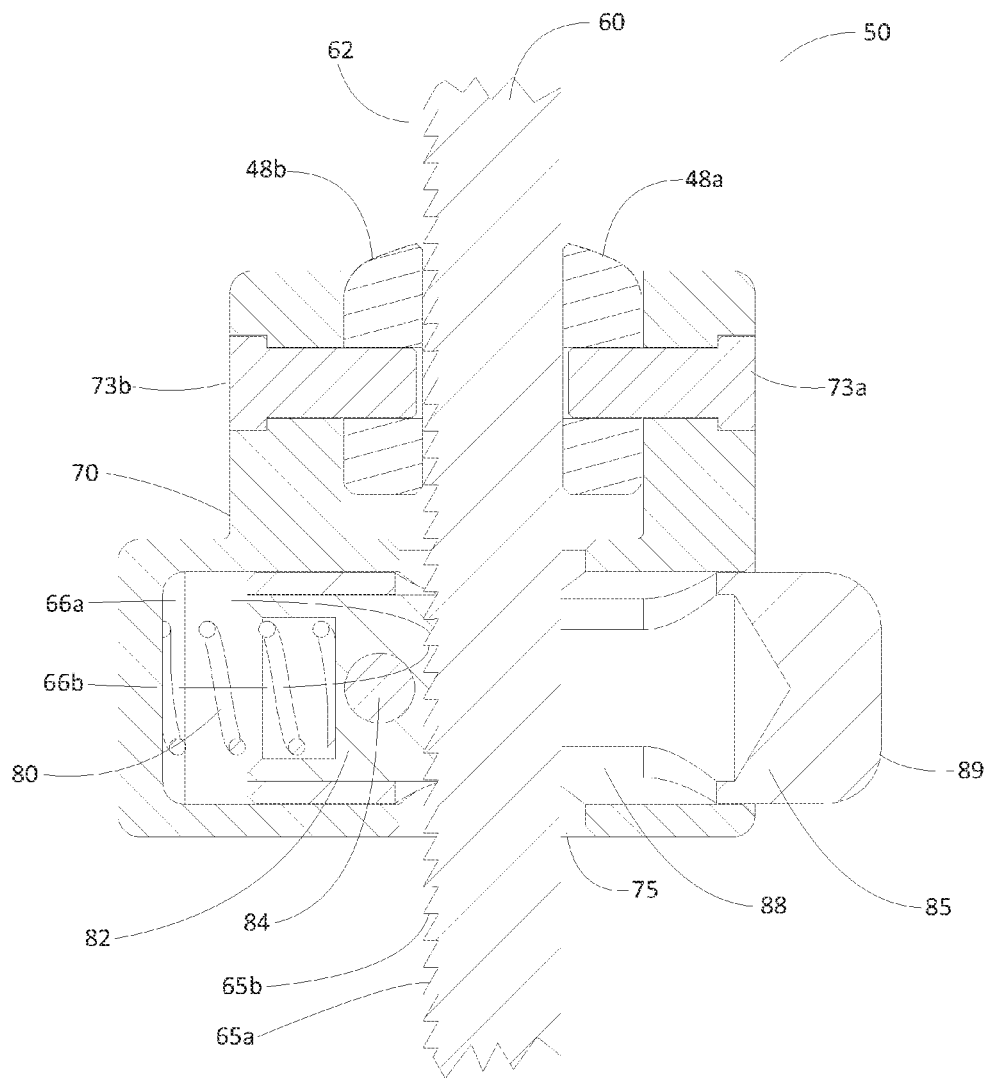
FIGS. 7a and 7b illustrate an exemplary locking release shaft with ratcheting mechanism in use.
Figure 7B:
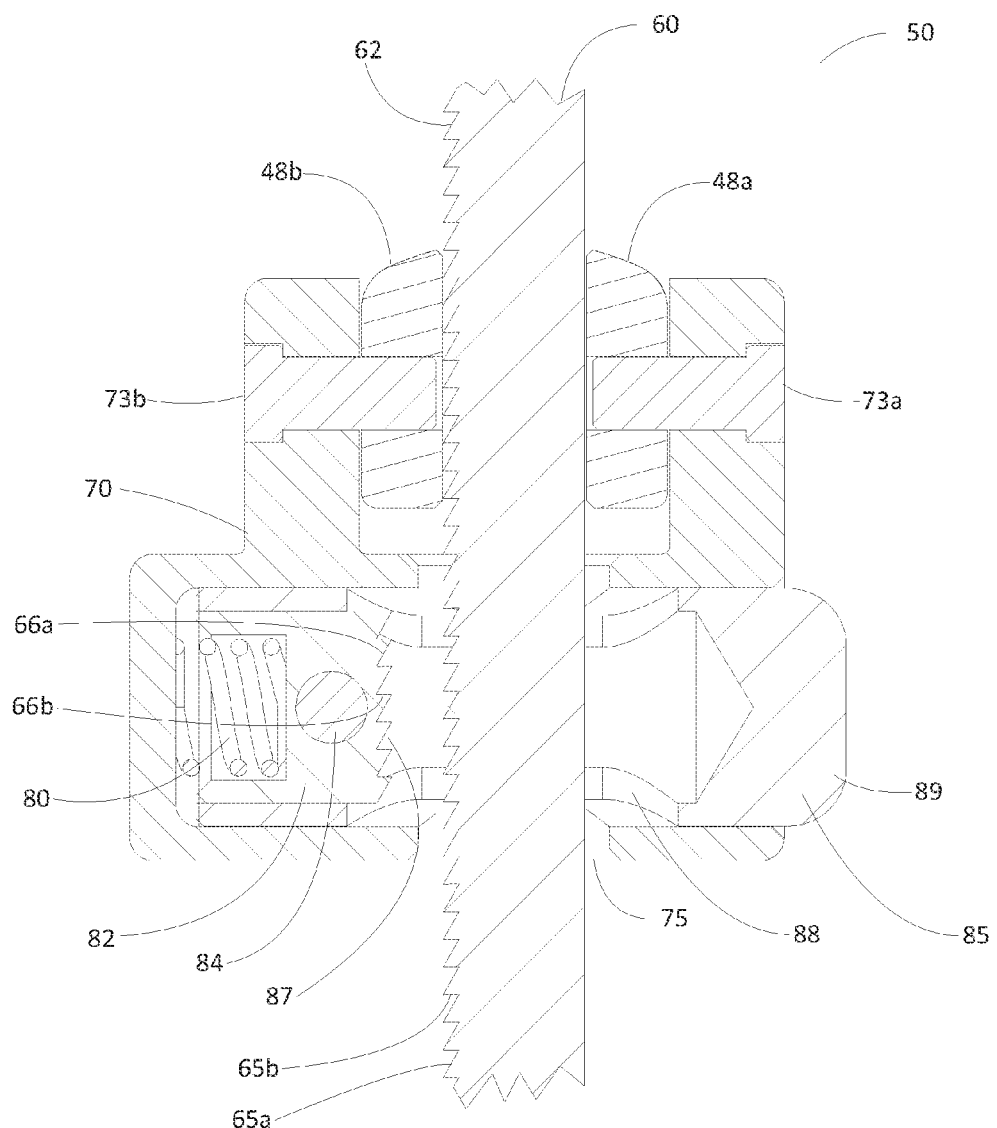

FIGS. 7a and 7b show the precision locking provided by ratcheting mechanism 50. In the exemplary embodiment shown, pawl device 70 is pivotally secured to gripping device 100 (not shown) at arms 48a, 48b by pins 73a, 73b, respectively. Post 60 passes between arms 48a, 48b and through pawl device 70 at aperture 75 and locking release shaft 85 at oblong aperture 88.

Pin 84 secures teeth-engaging structure 82 within locking release shaft 85, with teeth 87 corresponding to teeth 62 of post 60. Spring 80 is contained within pawl device 70 by locking release shaft 85 and teeth-engaging structure 82.

FIG. 7a illustrates ratcheting mechanism 50 at rest. Spring 80 provides an outward force against teeth-engaging structure 82, and therefore locking release shaft 85, keeping release surface 89 exposed and outward from pawl device 70 and post 60 against the teeth-engaging structure side of oblong aperture 88. Teeth 87 of teeth-engaging structure 82 engage teeth 62 of post 60, serving the dual purpose of preventing locking release shaft 85 from disengaging pawl device 70 and keeping gripping device 100 (not shown) locked in a tightening position.

As lower arm 30 (not shown) and upper arm 40 (not shown) are squeezed together to more tightly close gripping head 10 (not shown), post 60 is forced upward relative to pawl device 70. The angle of teeth 87 and 62 allow post 60 to slide freely within pawl device 70 only in that upward direction. Teeth 62 and 87 each include a plurality of angled portions 65a, 66a and flat surfaces 65b, 66b, respectively. Post 60 may slide freely in the upward direction through pawl device 70 because angled portions 65a, 66a slide against each other.

When lower arm 30 (not shown) and upper arm 40 (not shown) are forced away from each other (i.e., post 60 is forced downward relative to pawl device 70), flat surfaces 65b, 66b of teeth 87, 62, respectively, are forced against each other, and post 60 is prevented from moving within pawl device 70. Gripping device 100 (not shown) is therefore prevented from releasing an object being gripped, and may only be manipulated to close more tightly on the object being gripped.

As illustrated in FIG. 7a, multiple teeth 62 on post 60 are engaging teeth 87 of teeth-engaging structure 82. Each tooth 87 is in physical contact with a corresponding tooth 62 of post 60. By engaging multiple teeth 62, 87, a stronger locking force is created. In some exemplary embodiments, teeth-engaging structure 82 may contain more or fewer teeth 87 which engage teeth 62 of post 60. As post 60 is moved within pawl device 70, teeth 87 of teeth-engaging structure 82 engage different teeth 62 of post 60. At the extremities of post 60, teeth 87 of teeth-engaging structure 82 may engage fewer teeth 62 of post 60, such as, for example, when a portion of post 60 not containing teeth 62 is within pawl device 70.

The forces on teeth 87 and 62 are also perpendicular to each other. As post 60 is moved up or down relative to pawl device 70, teeth-engaging structure 82 is forced perpendicularly against post 60 by spring 80. The perpendicular motion of post 60 and teeth-engaging structure 82 relative to each other creates a strong and secure lock.

FIG. 7b illustrates the release of ratcheting mechanism 50 to allow post 60 to move downward relative to pawl device 70. As illustrated in the exemplary embodiment shown, release surface 89 is pressed inward, causing locking release shaft 85 to move inward and compress spring 80. Post 60 is no longer aligned along the portion of oblong aperture 88 aligned with teeth-engaging structure 82, and teeth 87 are no longer engaged with teeth 62. Post 60 may therefore move freely in either direction within pawl device 70.

In the exemplary embodiments shown in FIGS. 7a and 7b, the angled portions

Figure 8B:
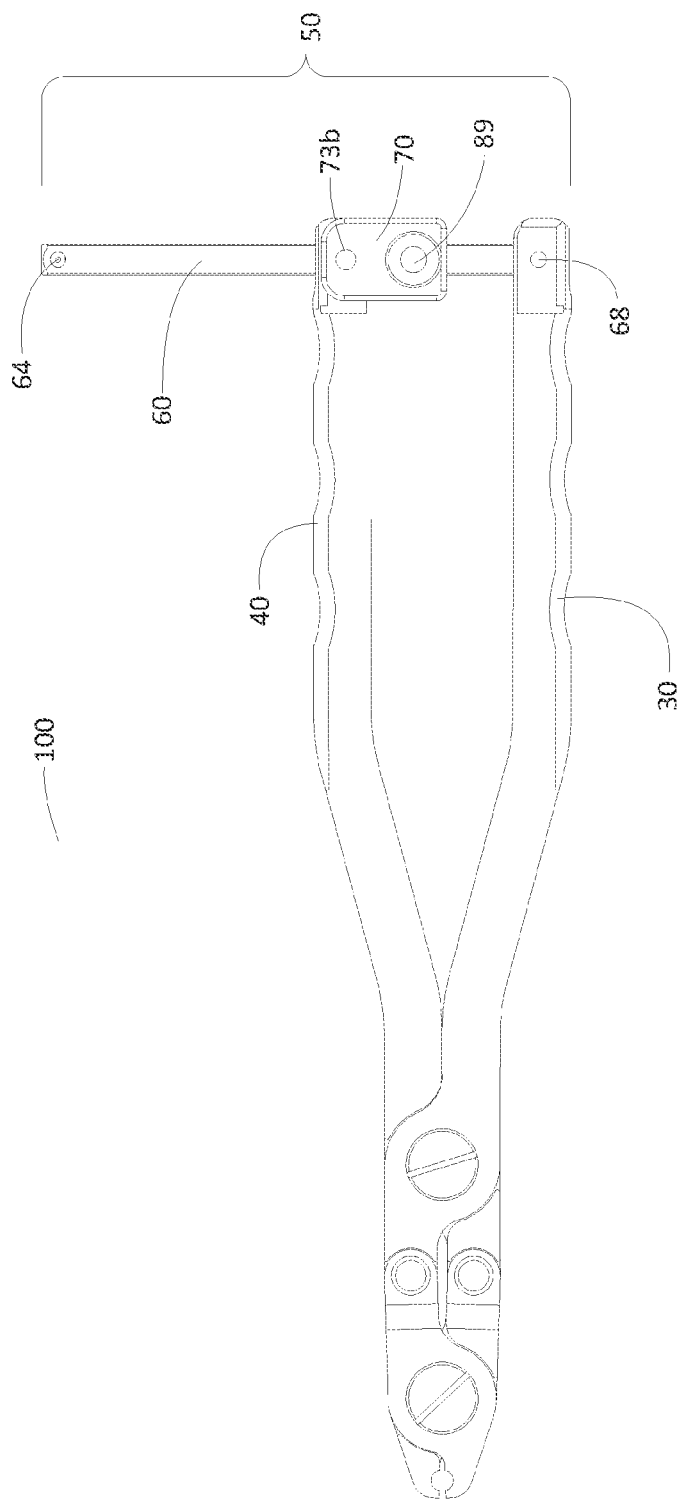
FIG. 8b illustrates an exemplary gripping device in closed position.

FIGS. 8a and 8b illustrate an exemplary gripping device 100 in its fully open and fully closed positions, respectively. As illustrated in FIG. 8a, gripping device 100 is fully open, with upper arm 40 fully extended upwards and pin 64 preventing post 60 from disengaging upper arm 40. Pins 73a (not shown) and 73b pivotally secure pawl device 70 to upper arm 40, while pin 68 pivotally secures post 60 to lower arm 30.

In the exemplary embodiment shown in FIG. 8a, post 60 and pawl device 70 are perpendicular to each other, but not to arms 30, 40. It is essential that pawl device 70 and post 60 are pivotally secured to upper arm 40 and lower arm 30, respectively, to ensure post 60 and pawl device 70 are always perpendicular to each other. Ratcheting mechanism 50 will not work if post 60 and pawl device 70 are not perpendicular.

As arms 30, 40 are pushed towards each other to close gripping device 100, post 60 and pawl device 70 pivot relative to arms 30, 40, respectively, to remain perpendicular to each other. As a result, as illustrated in FIG. 8b, post 60 and pawl device 70, as well as arms 30, 40 reach a point where they are all in perpendicular alignment.

What is claimed is:

1. A gripping device comprising:
   an upper arm and a lower arm, each terminating at one end in a gripping head and at the other in a U-shaped receiver, wherein said arms are pivotally connected at two pivotal joints, and wherein each of arms further include a hinged joint between said pivotal joints;
   a ratcheting mechanism pivotally connected to said U-shaped receivers and joining said upper arm and said lower arm, wherein said ratcheting mechanism is comprised of
   a post having a plurality of teeth between an upper end and a lower end, wherein said lower end is pivotally connected to said lower arm at said U-shaped receiver,
   a pawl device connected to said upper arm at said U-shaped receiver and having a central hollow cavity with an aperture,
   a locking release shaft having an oblong aperture corresponding to said aperture of said pawl device and release surface, said locking release shaft housed within said pawl device such that said release surface projects from said pawl device,
   a teeth-engaging structure having a plurality of teeth corresponding to said teeth of said post and housed within said locking release shaft,
   a spring housed within said pawl device and exerting an outward force on said teeth-engaging structure to keep release surface projecting from said pawl device and said teeth of said teeth-engaging structure engaged with said teeth of said post,
   wherein inward pressure against said release surface compresses said spring to disengage said teeth-engaging structure from said post to allow said post to slide freely through said oblong aperture of said locking release shaft and said aperture of said pawl device,
   wherein said outward force exerted by said spring is perpendicular relative to the sliding motion of said post, and
   wherein at least one of said plurality of teeth on said post is in physical engaging contact with at least one of said plurality of teeth on said teeth-engaging structure.

2. The device of claim 1 wherein said teeth of said post and said teeth of said teeth-engaging structure each contain an angled portion and a flat surface.

3. The device of claim 2 wherein said angled portions of said teeth of said post angle downward and said angled portions of said teeth of said teeth-engaging structure angle upward.

4. The device of claim 1 wherein a plurality of teeth on said post are in physical engaging contact with a plurality of teeth on said teeth-engaging structure.

5. The device of claim 1 wherein said plurality of teeth on said post cover the lower two-thirds of said post.

6. The device of claim 1 wherein said post is pivotally connected between the arms of said U-shaped receiver of said lower arm.

7. The device of claim 1 wherein said pawl device is connected to the outer surface of the arms of said U-shaped receiver of said upper arm.

8. The device of claim 1 wherein said teeth-engaging structure is secured in said locking release shaft with a pin.

9. The device of claim 1 wherein said upper arm and said lower arm each include at least one gripping surface.

10. The apparatus of claim 1 wherein said U-shaped receivers are parallel with each other and said post and said pawl device are perpendicular to each other when said apparatus is in a closed position.

11. The apparatus of claim 1 wherein said U-shaped receivers are not parallel with each other and said post and said pawl device are perpendicular to each other when said apparatus is in an open position.

12. A gripping apparatus with a precision ratcheting mechanism comprised of:
an upper arm having a bend, terminating at a first end in a gripping head and at a second end in a U-shaped receiver and including a hinged joint;
a lower arm having a bend, terminating at a first end in a gripping head and at a second end in a U-shaped receiver and including a hinged joint;
wherein said U-shaped receivers each include two parallel arms with apertures;
at least two pivotal joints joining said upper arm and said lower arm with said griping heads aligned and said hinged joint on said lower arm sits above said hinged joint on said upper arm, wherein said pivotal joints are positioned with said hinged joints between said pivotal points;
a pawl device comprised of
a U-shaped housing defining a cavity and having two apertures corresponding to said apertures on said arms of said U-shaped receiver of said upper arm,
wherein said U-shaped housing has an upper aperture and a lower aperture providing a passage through said cavity and a side aperture,
two pins adapted to engage said apertures on said U-shaped housing and said corresponding apertures on said U-shaped receiver of said upper arm to connect said pawl device to said upper arm,
a tubular locking release shaft having an upper oblong aperture and lower oblong aperture providing a passage through said locking release shaft, a side aperture and a release surface,
a teeth-engaging structure having a plurality of teeth and positioned within said tubular locking release shaft,
a spring compressed within said U-shaped housing against said teeth-engaging structure,
a post with an upper end, a lower end, and at least one flat surface containing a plurality of teeth corresponding to said teeth of said teeth-engaging structure, wherein said lower end contains an aperture corresponding to said apertures of said arms of said U-shaped receiver on said lower arm,
wherein said post is pivotally connected to said lower arm by a pin passing through said apertures in said U-shaped receiver of said lower arm and said aperture in said lower end of said post so that said flat surface containing a plurality of teeth is facing said teeth-engaging structure,
wherein said post passes between said arms of said U-shaped receiver of said upper arm and through said upper aperture of said U-shaped housing, said upper oblong aperture of said tubular locking release shaft, said lower oblong aperture of said tubular locking release shaft, and said lower aperture of said U-shaped housing,
wherein said spring exerts pressure on said teeth-engaging structure causing at least one of said plurality of teeth of said teeth-engaging structure to engage at least one of said plurality of teeth of said post,
wherein said pressure exerted by said spring is perpendicular to the movement of said post, and
wherein inward pressure against said release surface compresses said spring to disengage said teeth-engaging structure from said post to allow said post to slide freely through said oblong aperture of said locking release shaft and said aperture of said pawl device.

13. The apparatus of claim 12 wherein said teeth of said post and said teeth of said teeth-engaging structure each contain an angled portion and a flat surface.

14. The apparatus of claim 13 wherein said angled portions of said teeth of said post angle downward and said angled portions of said teeth of said teeth-engaging structure angle upward.

15. The apparatus of claim 12 wherein said upper arm and said lower arm each include at least one gripping surface.

16. The apparatus of claim 12 wherein said U-shaped receivers are parallel with each other and said post and said pawl device are perpendicular to each other when said apparatus is in a closed position.

17. The apparatus of claim 12 wherein said U-shaped receivers are not parallel with each other and said post and said pawl device are perpendicular to each other when said apparatus is in an open position.

18. The apparatus of claim 12 wherein said plurality of teeth on said post cover at least half of the lower surface of said flat surface.

19. The apparatus of claim 12 wherein more than one of said plurality of teeth on said post engage more than one of said plurality of teeth on said teeth-engaging structure.

20. The apparatus of claim 12 wherein said teeth-engaging structure and said locking release shaft each have a corresponding aperture through which a pin protrudes to secure said teeth-engaging structure in said locking release shaft.

* * * * *